United States Patent [19]
Kirov et al.

[11] Patent Number: 5,492,013
[45] Date of Patent: Feb. 20, 1996

[54] METHOD AND APPARATUS FOR ACOUSTIC TESTING OF ARMATURES

[75] Inventors: Dalibor Kirov; Giuseppe Cardini, both of Florence, Italy

[73] Assignee: Axis USA, Inc., Tampa, Fla.

[21] Appl. No.: 170,427

[22] Filed: Dec. 20, 1993

[51] Int. Cl.$^6$ ............................................. G01N 29/04
[52] U.S. Cl. ............................ 73/600; 73/588; 73/582
[58] Field of Search ............................. 73/588, 600, 644, 73/579, 582, 629; 340/682, 683; 367/13, 87

[56] References Cited

U.S. PATENT DOCUMENTS

| | | | |
|---|---|---|---|
| 4,642,617 | 2/1987 | Thomas | 340/683 |
| 4,655,084 | 4/1987 | Renzel | 73/600 |
| 4,707,687 | 11/1987 | Thomas | 340/683 |
| 4,862,383 | 8/1989 | Koshimizu | 73/600 |

Primary Examiner—Hezron E. Williams
Assistant Examiner—Christine K. Oda
Attorney, Agent, or Firm—Fish & Neave; Jeffrey H. Ingerman

[57] ABSTRACT

An objective and non-destructive test of the fused tang/commutator bar joints in an armature, that can be used on every armature being manufactured on an armature manufacturing line, as well as apparatus for performing that test, are provided. The armature is immersed in an acoustic coupling medium. Acoustic pulses, preferably ultrasonic pulses, are beamed onto the joint and the reflected pulses are measured. The quality of the joint can be determined by comparing the reflected amplitude to the known reflected amplitudes for joints of known quality. A testing station on an armature production line includes a mechanism for removing the armature from the production line, immersing it in the coupling medium, and rotating it as each joint in the commutator of that armature is checked.

52 Claims, 6 Drawing Sheets

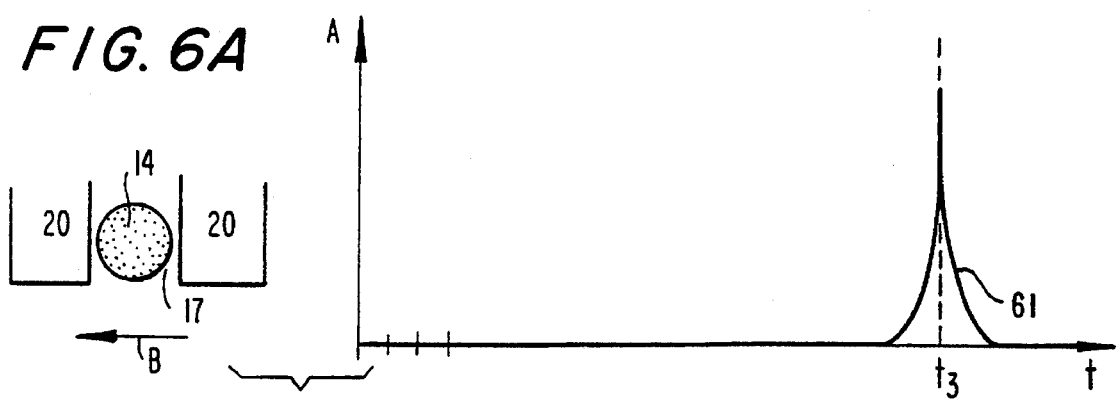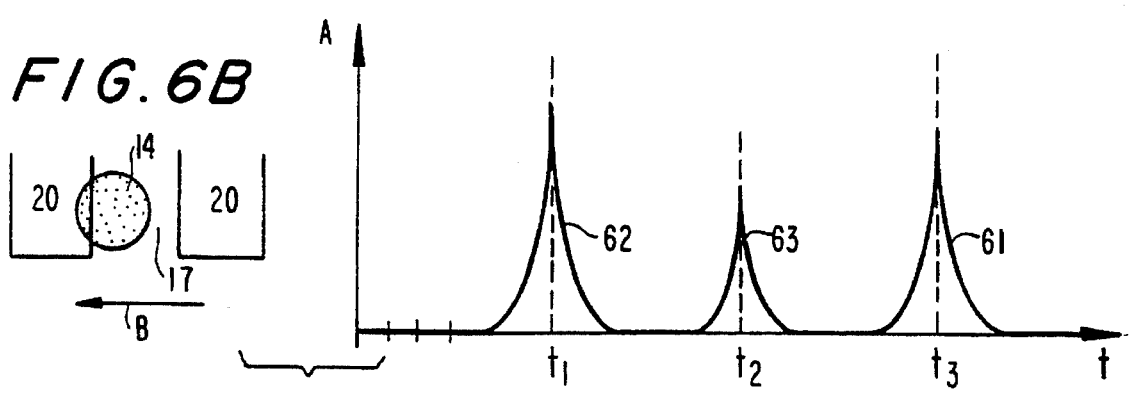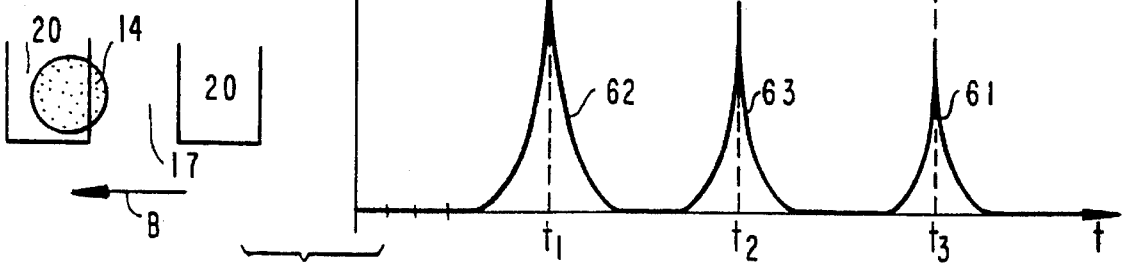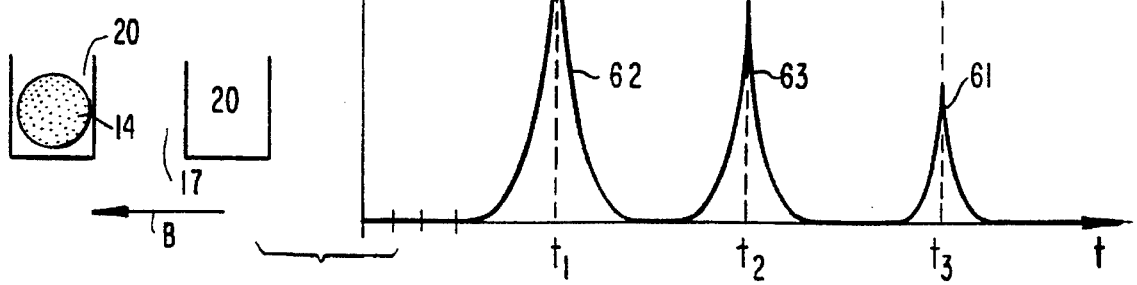

METHOD AND APPARATUS FOR ACOUSTIC TESTING OF ARMATURES

BACKGROUND OF THE INVENTION

This invention relates to the acoustic testing of armatures of dynamoelectric machines. More particularly, this invention relates to the ultrasonic testing of fused joints between the tangs and commutator bars of such an armature.

The armature of a dynamoelectric machine—i.e., of an electric motor or generator—has at least one wire coil wound thereon. Electrical power is conducted to the coils through a commutator which circumscribes the armature shaft and contacts electrical brushes on the stationary part of the dynamoelectric machine. The commutator is made of an even number of commutator "bars" spaced around the shaft. Each end of each coil terminates at a commutator bar.

A commutator bar is generally a substantially rectangular piece of copper. If the number of commutator bars in the commutator is small, each bar may have a slight curvature so that the commutator as a whole is substantially round. Where the number of commutator bars is large, it is not necessary for the bars to be curved.

A commonly employed method for terminating the coil end leads to the commutator bars is to provide on each commutator bar a small finger-like extension known as a "tang." The tang is bent at an angle to form a hook around which the coil lead is wrapped. The tang is then bent over parallel to and touching the commutator bar, so that the lead is trapped. The surfaces of the tang and the commutator bar that are in contact are then joined to prevent the tang from unfolding and freeing the lead.

A common method of joining the tang surface to the commutator bar surface is called "fusing" or "hot-staking." In this method, the surfaces are joined by applying pressure on the tang with a probe, forcing the tang against the commutator bar, and then heating the joint by either heating the probe or passing an electric current from the probe through the joint. The combination of heat and pressure causes projections and depressions on one surface to interengage with depressions and projections on the other surface to form a frictional joint; no significant melting of either surface occurs. In addition, an insulating coating on the wire trapped in the joint vaporizes, allowing the wire to make electrical contact with the commutator bar.

Because of the nature of fusing, fused joints will almost always contain gaps. Usually, these gaps are small "microgaps" dispersed throughout the joint, but larger gaps could also be present. The number, size and distribution of gaps determines the quality of the fused joint. Joint quality can be measured, for example, by the percentage of the area of the joint that is occupied by gaps; the higher the percentage, the worse the joint.

In practice, however, it has not heretofore been possible to directly measure the gap percentage. Instead, a test known as the "click test" has commonly been used. In the click test, a mechanical probe is manually inserted into the joint by an operator who applies force to break the joint open. The breaking of the joint produces an audible click sound, and the operator is trained to distinguish the sound of a good joint from that of a bad joint. The test is thus highly subjective, leading to variations in quality depending on the operator's perceptions. In addition, the test is destructive, and tested armatures must be discarded. Statistical assumptions must be made with respect to untested armatures, which are the only ones that can be used.

In a refined version of the click test, the probe is equipped with a force gauge, and the force needed to break open the joint is measured. When the force exceeds a threshold, a good joint is indicated. Although this test is more objective, it is still destructive and must rely on statistical assumptions with respect to the untested armatures. Even if the application of force were stopped at some level deemed appropriate (assuming the joint has not opened at a lower level of force), thus saving the armature, such a test would be too slow to use on all armatures. Statistical assumptions would still be required.

Thus, it would be desirable to be able to provide an objective and non-destructive test of the fused tang/commutator bar joints in an armature.

It would also be desirable to be able to provide such a test that could be used, if desired, on every armature being manufactured on an armature manufacturing line.

SUMMARY OF THE INVENTION

It is an object of this invention to provide an objective and non-destructive test of the fused tang/commutator bar joints in an armature.

It is also an object of this invention to provide such a test that could be used, if desired, on every armature being manufactured on an armature manufacturing line.

In accordance with the present invention, there is provided a method for testing the quality of a fused joint between a commutator tang and a commutator bar in a commutator of an armature of a dynamoelectric machine, where the commutator bar has first and second opposed substantially parallel commutator bar surfaces, the tang has first and second opposed substantially parallel tang surfaces, and the fused joint is formed between the first commutator bar surface and the first tang surface. The method includes directing an acoustic beam toward the second tang surface along an axis substantially perpendicular to the second tang surface, at least a portion of the beam passing through the tang and reflecting off the joint. The reflected portion of the beam is measured to determine a reflected amplitude. The reflected amplitude is analyzed to derive an indication of the quality of the joint.

Apparatus for carrying out the method, as well as an armature testing station incorporating the apparatus, are also provided.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout, and in which:

FIGS. 6A–6D are schematic representations of the acoustic beam of the present invention as it scans different locations between two adjacent joints, showing graphical representations of the acoustic signals reflected at each location;

DETAILED DESCRIPTION OF THE INVENTION

Figure 1:
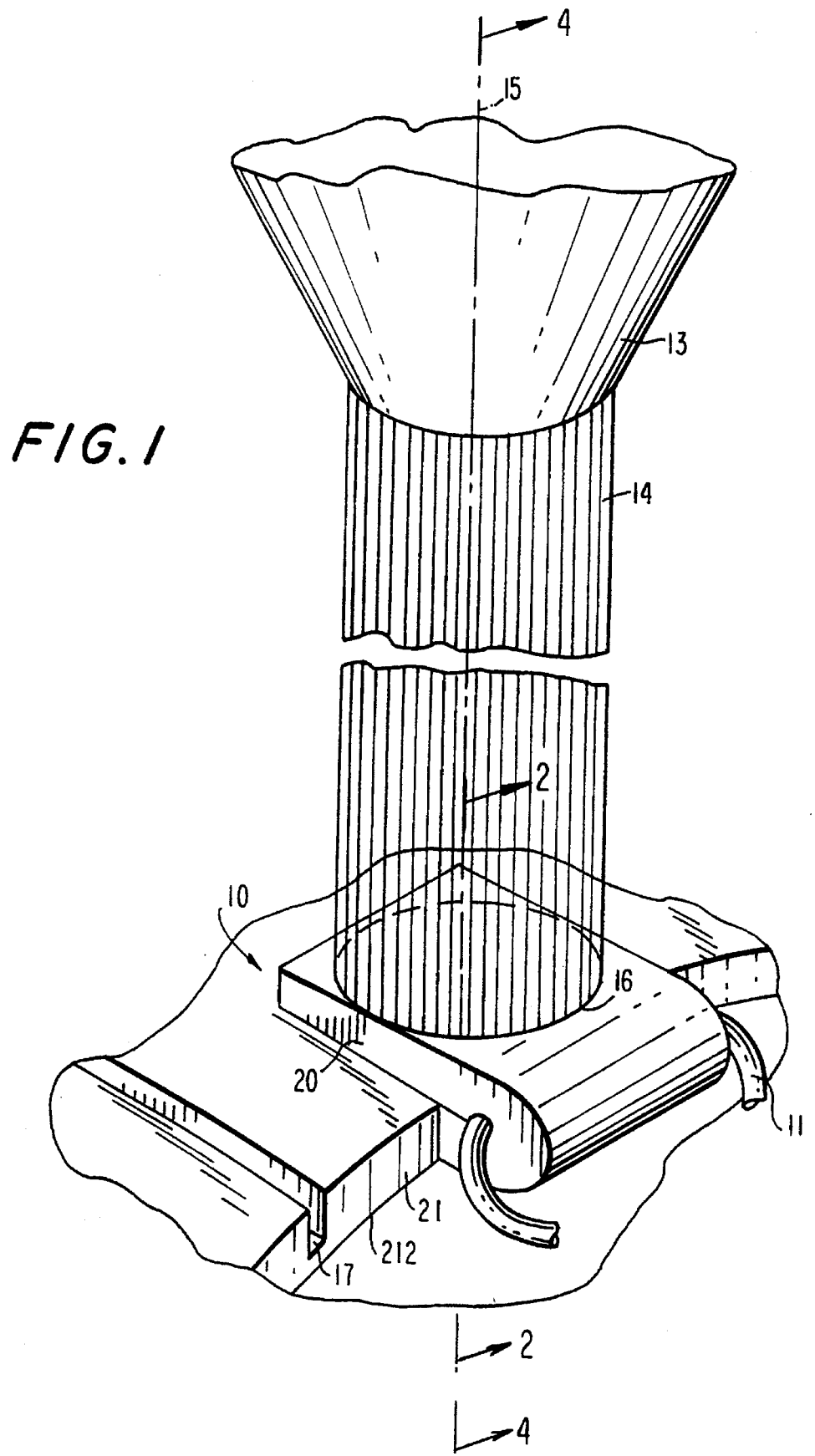
FIG. 1 is a fragmentary perspective view of a fused tang/commutator joint being tested in accordance with the present invention.

The present invention uses an acoustic beam, preferably an ultrasonic beam, to test fused tang/commutator joints. The quality of the joint is determined by measuring the reflection of the ultrasonic beam from the joint.

As discussed above, a fused joint is formed by the interlocking of the projections and depressions in the surfaces being joined. In a theoretically "perfect" joint, every projection finds a depression to fill, and every depression is filled by a projection, with no gaps whatsoever in the structure. Such a joint would appear to the ultrasonic beam as a continuous mass of metal, and as such would be transparent to the beam, generating no reflection. At the other extreme, the worst possible joint is one which is completely open. Such a joint would reflect a maximum amount of the beam, producing a maximum reflected amplitude, although because of attenuation, the reflected amplitude received at the probe would not be expected equal the amplitude of the original beam transmitted from the probe, even if 100% of the beam were reflected.

In practice, actual fused joints are neither theoretically perfect, nor are they open. Instead, they contain some percentage of gaps or unjoined areas. Thus, the reflected beam amplitude will range between above about zero and below about the original amplitude; the more gaps there are in the joint, the greater the reflected amplitude will be.

In fact, even a joint considered "perfect," or the best attainable joint, in practice, may contain some open area. Specifically, for certain types of tangs, it may be possible to achieve a joint with no measurable open area, other than microgaps. However, for other types of tangs, there may be about 25% open area—i.e., the two sides of the joint are not touching in approximately 25% of the area of the joint as measured in the plane of the joint. For still other types of tangs, the joint may have a different amount of open area. It has been found empirically that a joint can have up to about 75% open area and still be acceptable. It has also been found empirically that the amplitude of the reflected signal can be made directly proportional to the open area.

Specifically, at a preferred frequency of about 20 MHz, for a particular type of copper tang of the size used in small electric motors, measured in the acoustic coupling medium described below, the reflected amplitude has been found to be directly proportional to the amount of open area resulting from gaps having a depth greater than about 0.005 mm perpendicular to the plane of the joint. Although there may also be microgaps having a depth less than about 0.005 mm that do not contribute significantly to the reflected amplitude, such microgaps are not of concern in assessing the quality of the joint, and thus the reflected amplitude can be used as a measure of the open area.

By measuring a known "perfect" joint, one can obtain a minimum expected reflected amplitude (corresponding to the amount of open area). Similarly, by measuring a totally open joint, one can obtain a maximum expected reflected amplitude (corresponding to about 100% open area). For gaps of interest (i.e., those greater in depth than about 0.005 mm when a probe frequency of 20 MHz is used for the particular type of tang discussed above), the gap area, or open area, can be determined by linearly interpolating the reflected amplitude between the minimum and maximum expected amplitudes.

In testing apparatus according to the invention, it is preferred that an ultrasonic probe having both a transmitter and a receiver be used. The probe would be aimed at the outer surface of the tang along an axis substantially perpendicular to the outer surface of the tang (and to the joint) so that the reflection returns to the receiver in the probe. Such probes are available in both focused and unfocused varieties, with the difference for purposes of the present invention being in how far from the test area the probe can be and still be focused on the tang without spilling onto adjacent areas. An unfocused probe can be further from the surface than a focused probe. A preferred probe is a focused probe because it is easier to align the probe perpendicularly to the joint when it is closer to the test area.

It is also preferred that the probe and the test sample be immersed in a medium having an acoustic conductivity higher than that of air, for better coupling of the beam to the sample. The acoustic coupling medium should also preferably be electrically nonconductive so that any residue that may remain on the sample does not adversely affect performance of the dynamoelectric machine in which it is installed. Similarly, the acoustic coupling medium preferably should not oxidize any part of the armature. One particularly preferred medium is sold as an environmentally safe cleaning and degreasing agent for electrical and electronic components under the name "KEMPT" by the Chemsearch division of NCH, of Milan, Italy.

The selection of a frequency for the probe beam depends on the area and depth of the gaps expected in the joints to be tested, the material of the tang, the thickness of the tang, and the coupling medium. As set forth above, a frequency of about 20 MHz is preferred for one particular type of copper tang used in small electric motors, tested in the KEMPT medium described above.

A preferred embodiment of a testing station on an armature production line, for testing tang/commutator joints in accordance with the present invention, would have a device, such as a collet mechanism, for removing the armature to be tested from the production line conveyor and placing it in a vessel filled with acoustic coupling medium. The ultrasonic probe preferably would already be in the vessel. The collet mechanism would be adjusted so that the armature is inserted in the vessel with the surface of a tang, the joint of which is to be tested, aligned perpendicularly to the axis of the probe. Preferably, the collet would be capable of rotating the armature, so that more than one, and preferably all, of the tang/commutator joints on an armature could be tested individually. Such a station could be used to test a fraction of the armatures produced by the production line, either at regular intervals or on a random basis, or could be used to test all of the armatures produced. In the latter case, if a single testing station operated too slowly to keep up with the remainder of the production line, a number of identical testing stations could be provided to operate in parallel. The advantages of testing all armatures, without resorting to statistical analysis, is apparent.

In any event, the testing station would relay its results to the production line control unit, which would take appropriate action. If all armatures were being tested, the appropriate action would be to divert any armature with substandard tang/commutator joints to a station at which it could be discarded, or re-fused using modified fusing parameters. The production line might also be stopped for adjustment, especially if more than one armature tested within a certain time period was determined to have substandard tang/commutator joints. If only certain armatures were being tested, the primary response to a series of substandard joints would be to stop the production line for adjustment.

Figure 2:
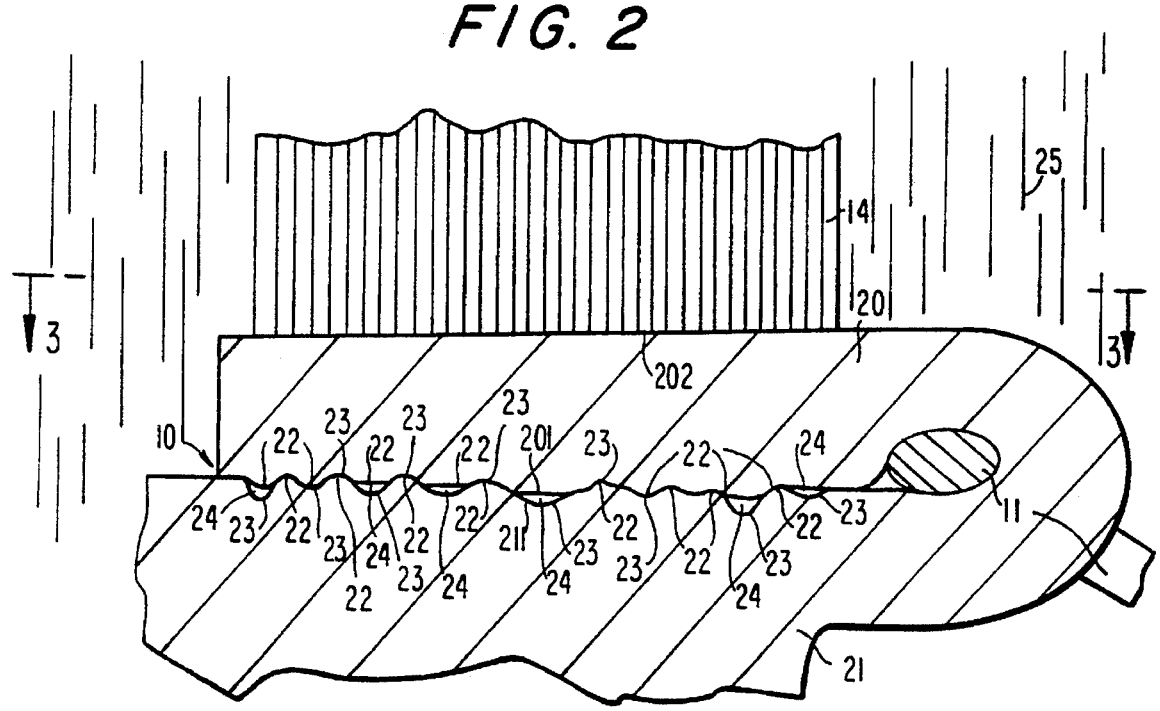
FIG. 2 is a cross-sectional view of a fused tang/commutator joint being tested in accordance with the present invention, taken from line 2—2 of FIG. 1.
Figure 3:
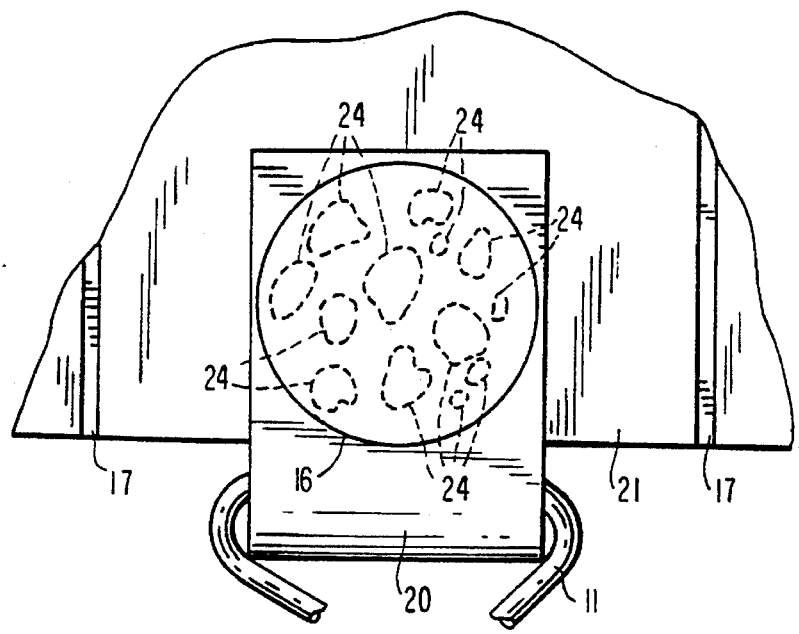
FIG. 3 is a plan view of a fused tang/commutator joint, taken from line 3—3 of FIG. 2.
Figure 4:
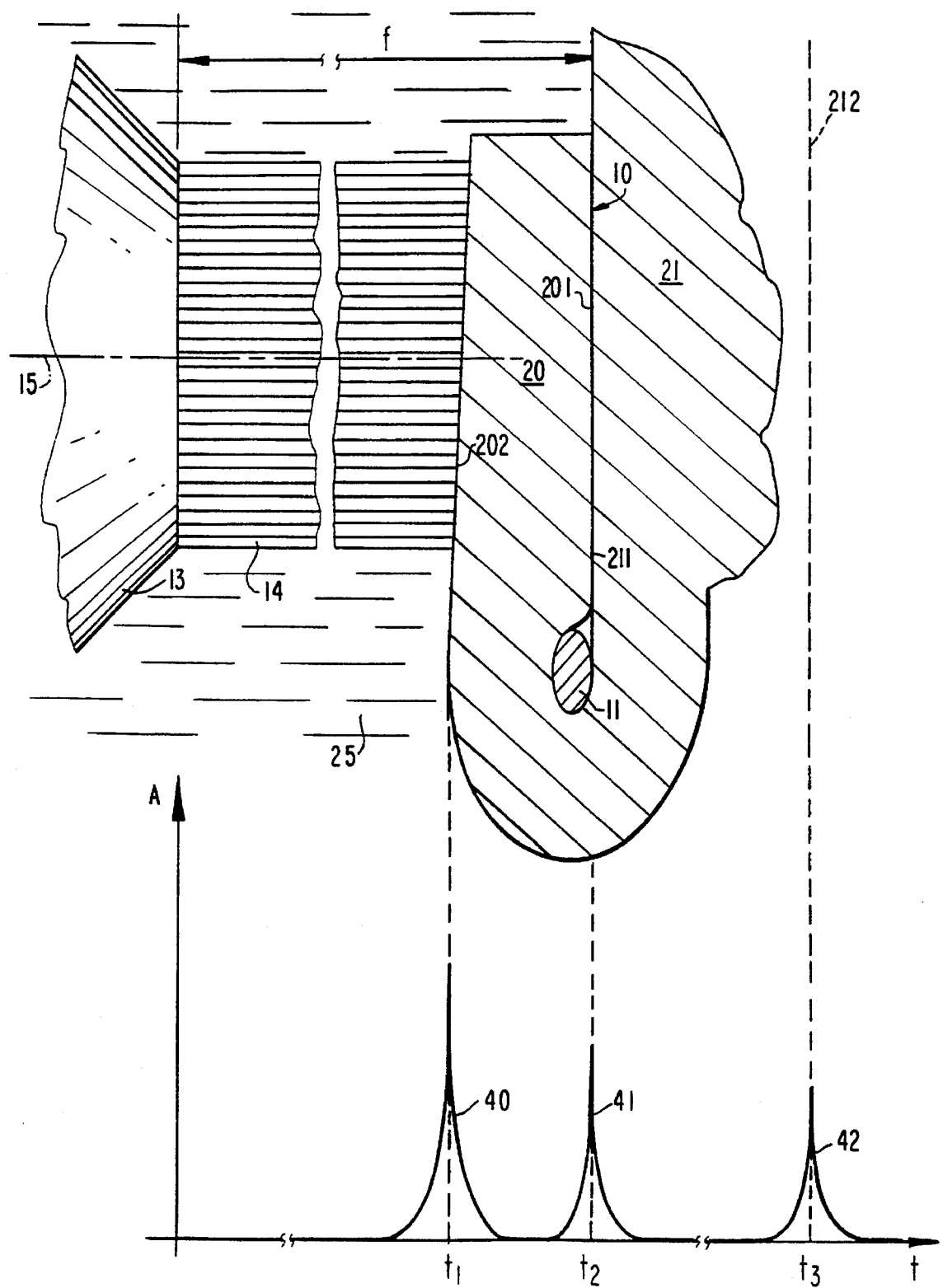
FIG. 4 is a fragmentary cross-sectional view of fused tang/commutator joint being tested in accordance with the present invention, taken from line 4—4 of FIG. 1, showing graphical representations of the acoustic signals reflected by the joint.
Figure 5:
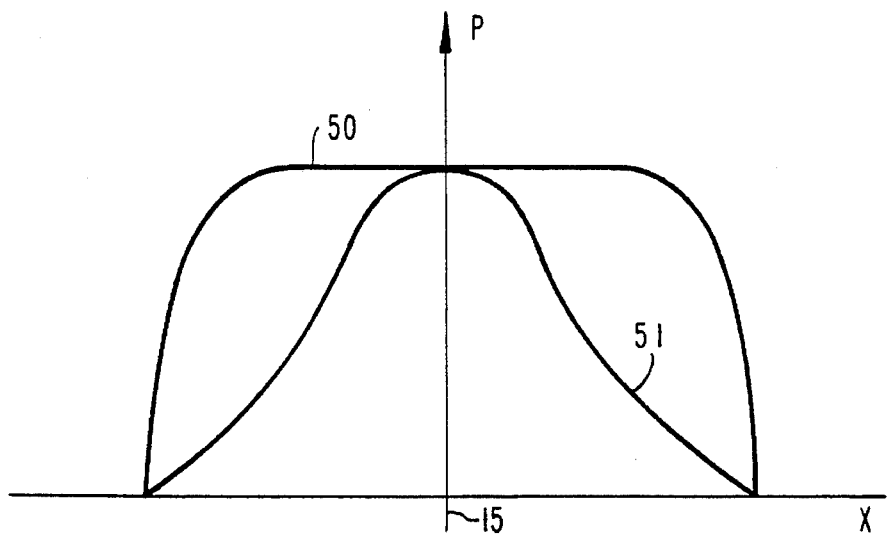
FIG. 5 is a graph showing the pressure distributions for two different acoustic probes of the type used in the present invention.

The theoretical principles of the present invention are illustrated in FIGS. 1–6D. A fused tang/commutator joint 10 to be tested is formed where tang 20 is folded over onto commutator bar 21 and first surface 201 of tang 20 is fused to first surface 211 of commutator bar 21. While both surfaces 201, 202 of tang 20, and both surfaces 211, 212 of commutator bar 21, appear to the naked eye to be smooth, as illustrated in FIGS. 1 and 4, they are in fact full of projections and depressions as illustrated in FIG. 2. The projections 22 and depressions 23, shown in exaggerated form in FIG. 2, interengage as described above to form joint 10, and also leave gaps 24 as described above (visible in FIG. 2 only). Wire 11 is captured in joint 10.

An ultrasonic probe 13 projects an ultrasonic beam 14 along an axis 15 substantially perpendicular to second tang surface 202. Probe 13 also contains a receiver. The spacing of probe 13 from joint 10, and the configuration of beam 14, are chosen so that the outer contour 16 of beam 14 falls entirely on joint 10, avoiding false echoes from the background 17. As discussed above, beam 14 preferably propagates through an acoustic coupling medium 25. Beam 14 is actually a series of acoustic pulses, each preferably having a pressure distribution about axis 15 as shown at 50 in FIG. 5, so that as strong a signal as possible is generated across the entire joint 10. A pressure distribution such as that shown at 51 is less preferred.

As shown in FIG. 4, the system of the invention transmits acoustic pulses at times spaced apart sufficiently for each pulse to return to probe 13 before the next pulse is sent. The spacing is based on the expected maximum round-trip time for a pulse. Each pulse in beam 14 is partially reflected by surface 202, giving rise to a detected pulse 40 at a time interval $t_1$ from the time of transmission, which is correlated to the distance between probe 13 and surface 202. Some portion of each pulse passes through surface 202 and reflects off gaps 24 in joint 10, giving rise to a detected pulse 41 at a time interval $t_2$ from the time of transmission, which is correlated to the distance between probe 13 and joint 10. Finally, some portion of each pulse passes through joint 10 (either because it impinges on joint 10 where there is no gap 24, or because a portion of the pulse impinging on gap 24 is able to pass through gap 24) and reflects off second surface 212 of commutator bar 21, giving rise to a detected pulse 42 at a time interval $t_3$ from the time of transmission, which is correlated to the distance between probe 13 and second surface 212. There are also effects caused by secondary reflections at each surface, but those can be ignored. The graph in FIG. 4 plots received amplitude A as a function of time t from transmission, with probe 13 spaced a distance f from joint 10, where f is the focal length of probe 13 (i.e., joint 10 lies in the focal plane of probe 13).

The effects of the various surfaces, as well as the need to have beam 14 aimed squarely at joint 10, is illustrated in FIGS. 6A–6D. In FIG. 6A, beam 14 is aimed at background 17 between two tangs 20. The corresponding plot 60 of reflected amplitude A versus time t shows a single pulse 61 corresponding to background 17. In FIG. 6B, beam 14 has moved in the direction of arrow B so that it partially impinges on one of tangs 20. In addition to pulse 61, whose amplitude is now diminished as other surfaces reduce the portion of beam 14 reaching surface 17, there are now pulses 61, 63 corresponding to surface 202 and joint 10. In FIG. 6C, beam 14 is almost completely aimed at one tang 20, and pulse 61 is further diminished while pulses 62, 63 have grown. Finally, in FIG. 6D, beam 14 is fully aimed at one tang 20, and pulses 61, 62, 63 have assumed the relative amplitudes seen in FIG. 4. Thus, it is important for accurate results that beam 14 be properly aimed. At the same time, the beam should not be limited to too small an area of joint 10, lest it miss too many of the gaps in the joint. Alternatively, a small beam could be used to separately measure small areas of the joint, and the individual reflected amplitudes could be integrated over the entire joint to give a reflected amplitude for the joint.

The peak of interest is peak 41, which represents the reflection off joint 10. As described above, minimum and maximum expected amplitudes of pulse 41 can be determined by calibrating a testing apparatus according to the invention against a known "perfect" joint (some known amount of open area) and a fully open joint (100% open area). For the conditions described above with respect to the material and thickness of tangs 20, the type of acoustic coupling medium used, and the acoustic frequency, the amplitude of pulse 41 is directly proportional to the amount of open area in joint 10, and thus the amount of open area can be determined by linear interpolation of the amplitude between the expected extrema. In practice, one may not be concerned with determining what the precise open area is. Instead, one may want to know merely whether the amount of open area is above or below a threshold deemed acceptable, so as to determine whether or not the quality of the joint is acceptable. This threshold would be determined by interpolation between the extrema based on the minimum acceptable open area.

Figure 7:
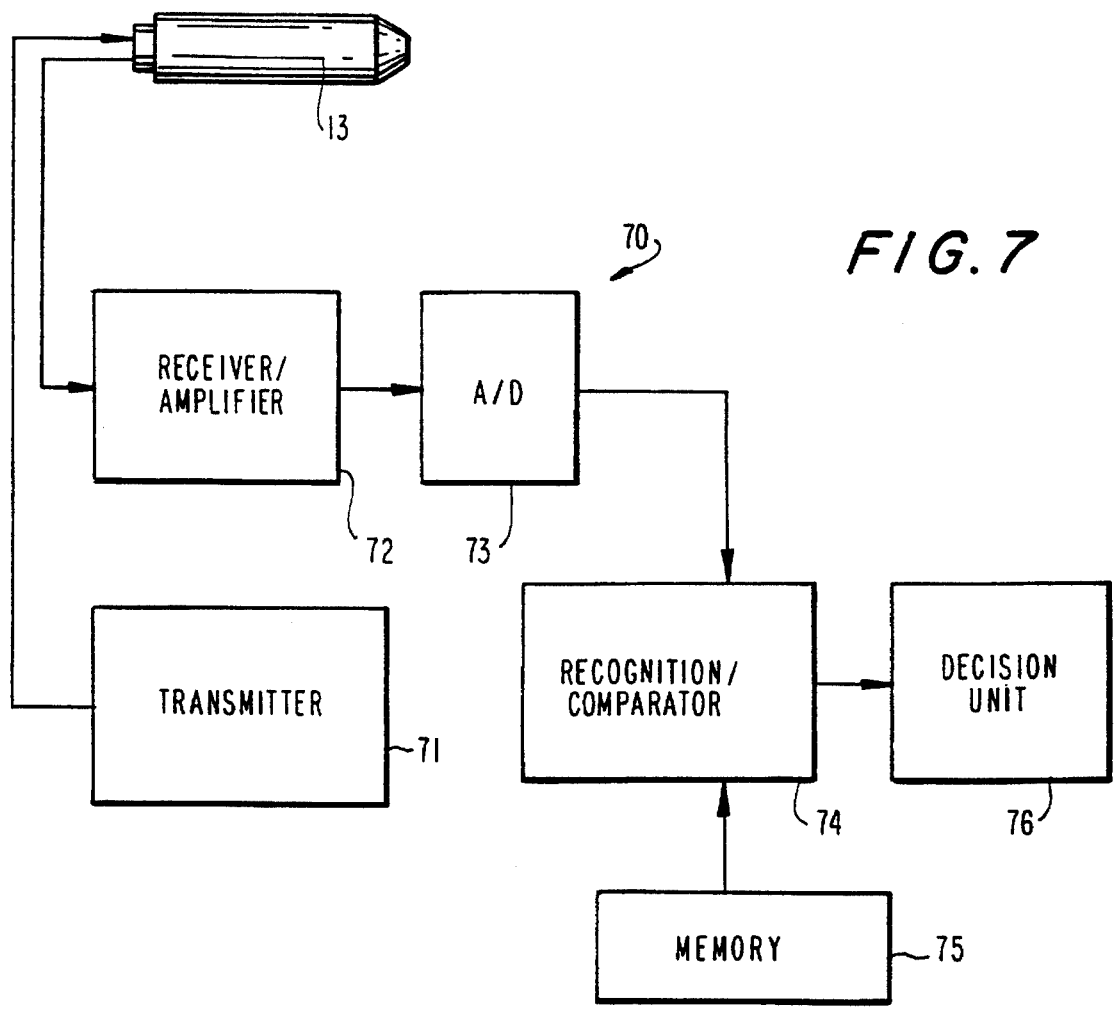
FIG. 7 is a schematic diagram of a preferred embodiment of testing apparatus according to the present invention.

A schematic diagram of apparatus 70 according to the invention is shown in FIG. 7. Apparatus 70 includes probe 13. A transmitter 71 supplies the ultrasonic or other acoustic pulses to be emitted by probe 13. The frequency of transmitter 71 is determined by the desired frequency to be emitted.

Reflected pulses received by probe 13 are fed to receiver/amplifier 72, which passes them through an analog-to-digital converter 73. The digital signal from A/D converter 73 is passed to recognition/comparator unit 74 which compares them, as described above, to signal patterns obtained from joints of known quality and stored in memory 75, or to a threshold stored in memory 75. The result of the comparison is passed to decision unit 76 which determines whether or not the joint is acceptable. As stated above, the output of unit 76 can be used to reject an armature, and discard it or require that it be re-fused.

Figure 8:
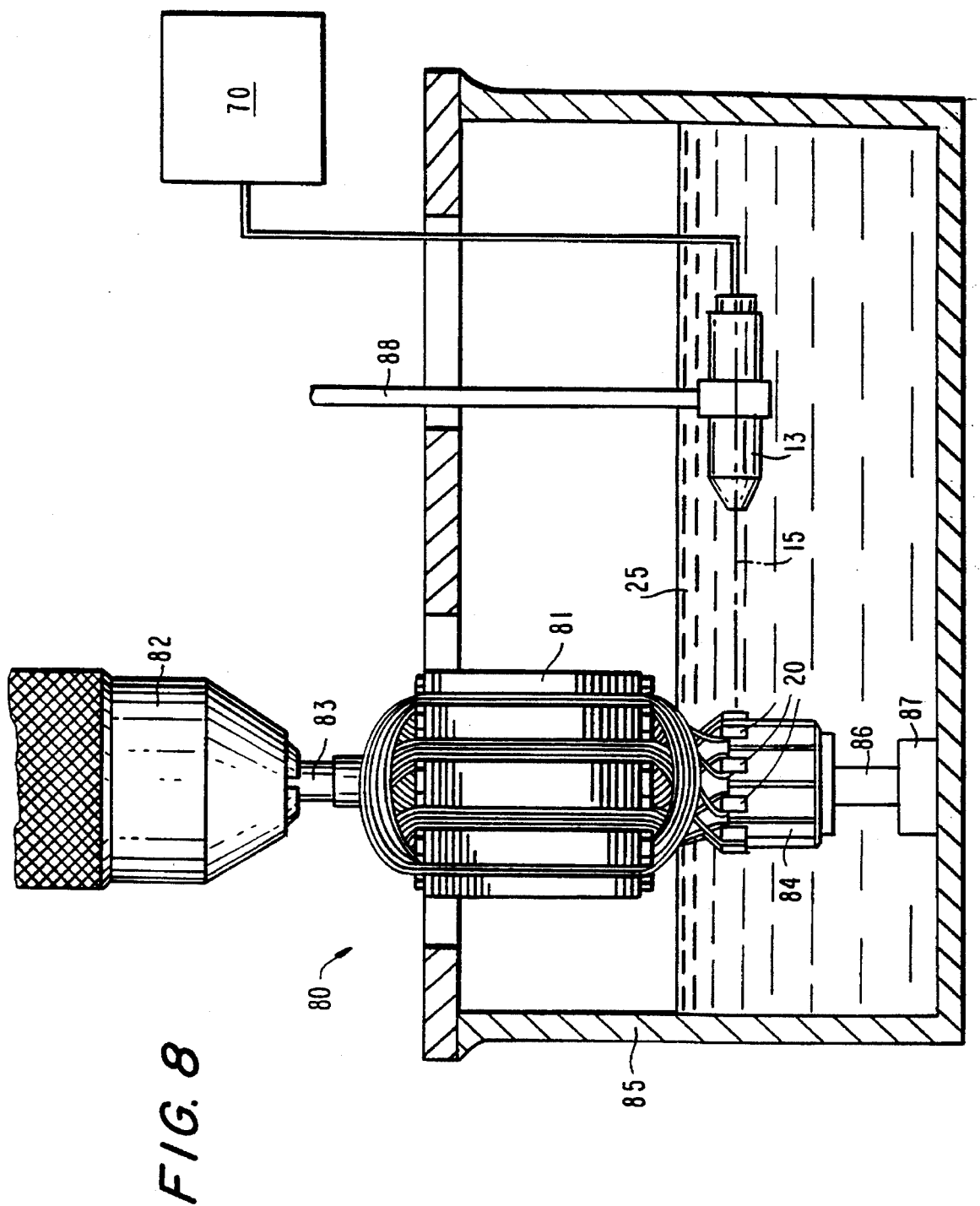
FIG. 8 is a side elevational view, partly in cross section, of a testing station according to the present invention.

An armature testing station 80 according to the invention for an armature production line is shown in FIG. 8. Armature 81 is removed from the production line conveyor (not shown) by collet mechanism 82 which engages end 83 of the armature shaft. Mechanism 82 immerses at least the commutator 84 of armature 81 in acoustic coupling medium 25 in a tank 85. The other end 86 of the armature shaft is rested in a support 87 at the bottom of tank 85. Probe 13 is suspended in tank 85 on arm 88, immersed in medium 25, and is connected by cable 89 to control circuitry 70. Arm 88 is preferably adjustable (not shown) so that axis 15 of probe 13 can be aligned with tangs 20 regardless of the size of armature 81. An appropriate aligning device (not shown) assures that the surface of one of tangs 20 is substantially perpendicular to axis 15.

Preferably, collet 82 is rotatable and support 87 allows rotation, so that armature 81 can be indexed to bring each of its tang/commutator joints in line with beam 14 for testing, as described above. Alternatively, instead of indexing armature 81, which adds time as rotation is stopped and started, armature 81 could be rotated continuously. In that case, beam 14 would scan over all the joints 10 in the manner shown in FIGS. 6A–6D. The peak at $t_2$, corresponding to joint quality, would rise and fall during the scanning process as joints moved in and out of beam 14. By monitoring the periodic maxima of the peak at $t_2$, one would be able to determine the quality for each joint, as long as one kept track of which maximum of the peak corresponded to which joint 10. Station 80 might also have more than one probe 13—e.g., three probes at 120° intervals around the armature—to shorten the time necessary to test all joints in a single armature. However, such an arrangement would increase the cost and complexity of station 80.

Thus it is seen that an objective and non-destructive test of the fused tang/commutator bar joints in an armature that can be used on every armature being manufactured on an armature manufacturing line, as well as apparatus for performing that test, are provided. One skilled in the art will appreciate that the present invention can be practiced by other than the described embodiments, which are presented for purposes of illustration and not of limitation, and the present invention is limited only by the claims which follow.

What is claimed is:

1. A method for testing the quality of a fused joint between a commutator tang and a commutator bar in a commutator of an armature of a dynamoelectric machine, said commutator bar having first and second opposed substantially parallel commutator bar surfaces, said tang having first and second opposed substantially parallel tang surfaces, said fused joint being formed between said first commutator bar surface and said first tang surface without melting any of said surfaces, said method comprising:

directing an acoustic beam comprising at least one acoustic pulse toward a portion of said second tang surface along an axis substantially perpendicular to said portion of said second tang surface, at least a portion of each said at least one pulse passing through said tang and reflecting off one or more gaps formed during fusing, said gaps being between said first commutator bar surface and said first tang surface at said joint;

measuring said reflected portion of each of said at least one pulse to determine a reflected amplitude of each of said at least one pulse; and analyzing said measured reflected amplitude to derive an indication of the quality of said joint, said quality of said joint being representative of the quantity and size of said gaps.

2. The method of claim 1 wherein said analyzing step comprises:

comparing said reflected amplitude to a threshold amplitude; and characterizing said joint as unacceptable if said reflected amplitude exceeds said threshold amplitude.

3. The method of claim 2 further comprising the steps of:

determining a minimum reflected amplitude by measuring said reflected amplitude for a joint known to be of maximum quality;

determining a maximum reflected amplitude by measuring said reflected amplitude for a joint known to be of minimum quality; and selecting said threshold amplitude, between said minimum reflected amplitude and said maximum reflected amplitude, to correspond to a desired quality between said minimum quality and said maximum quality.

4. The method of claim 1 wherein said step at directing an acoustic beam along said axis comprises directing an ultrasonic beam along said axis.

5. The method of claim 1 wherein said directing step comprises directing said beam toward said second tang surface through a medium having a greater acoustic conductivity than air.

6. The method of claim 5 wherein said directing step comprises directing said beam toward said second tang surface through a liquid medium.

7. The method of claim 6 wherein said directing step comprises directing said beam toward said second tang surface through a liquid medium that is substantially electrically nonconductive.

8. The method of claim 6 wherein said directing step comprises directing said beam toward said second tang surface through a liquid medium that is substantially non-oxidizing.

9. Apparatus for testing the quality of a fused joint between a commutator tang and a commutator bar in a commutator of an armature of a dynamoelectric machine, said commutator bar having first and second opposed substantially parallel commutator bar surfaces, said tang having first and second opposed substantially parallel tang surfaces, said fused joint being formed between said first commutator bar surface and said first tang surface without melting any of said surfaces, said apparatus comprising:

an acoustic beam emitter for directing an acoustic beam comprising at least one pulse toward a portion of said second tang surface along an axis substantially perpendicular to said portion of said second tang surface, at least a portion of each said pulse passing through said tang and reflecting off one or more gaps formed during fusing, said gaps being between said first commutator bar surface and said first tang surface at said joint;

an acoustic receiver for measuring said reflected portion of each of said at least one pulse to determine a reflected amplitude of each of said at least one pulse; and an analysis unit for deriving from said reflected amplitude an indication of the quality of said joint, said quality of said joint being representative of the quantity and size of said gaps.

10. The apparatus of claim 9 wherein said analysis unit compares said reflected amplitude to a threshold amplitude, and characterizes said joint as unacceptable if said reflected amplitude exceeds said threshold amplitude.

11. The apparatus of claim 10 wherein said threshold amplitude is calibrated by:

determining a minimum reflected amplitude by measuring said reflected amplitude for a joint known to be of maximum quality;

determining a maximum reflected amplitude by measuring said reflected amplitude for a joint known to be of minimum quality; and selecting said threshold amplitude, between said minimum reflected amplitude and said maximum reflected amplitude, to correspond to a desired quality between said minimum quality and said maximum quality.

12. The apparatus of claim 9 wherein said acoustic beam emitter is an ultrasonic beam emitter.

13. The apparatus of claim 9 further comprising a vessel containing a medium having a greater acoustic conductivity than air; wherein:

said joint, said emitter and said receiver are immersed in said medium.

14. The apparatus of claim 13 wherein said medium is a liquid.

15. The apparatus of claim 14 wherein said liquid medium is substantially electrically nonconductive.

16. The apparatus of claim 14 wherein said liquid medium is substantially non-oxidizing.

17. The apparatus of claim 9 wherein said acoustic beam emitter and said acoustic receiver are combined in an acoustic probe.

18. In a manufacturing line for dynamoelectric machine armatures, an armature testing station for testing the quality of a fused joint between a commutator tang and a commutator bar in a commutator of an armature, said commutator bar having first and second opposed substantially parallel commutator bar surfaces, said tang having first and second opposed substantially parallel tang surfaces, said fused joint being formed between said first commutator bar surface and said first tang surface without melting any of said surfaces, said armature testing station comprising:

an acoustic beam emitter for directing an acoustic beam comprising at least one acoustic pulse toward a portion of said second tang surface along an axis substantially perpendicular to said portion of said second tang surface, at least a portion of said at least one pulse passing through said tang and reflecting off one or more gaps formed during fusing, said gaps being between said first commutator bar surface and said first tang surface at said joint;

an acoustic receiver for measuring said reflected portion of each of said at least one pulse to determine a reflected amplitude of said pulse; and an analysis unit for deriving from said reflected amplitude an indication of the quality of said joint, said quality of said joint being representative of the quantity and size of said gaps.

19. The apparatus of claim 18 wherein said analysis unit compares said reflected amplitude to a threshold amplitude, and characterizes said joint as unacceptable if said reflected amplitude exceeds said threshold amplitude.

20. The armature testing station of claim 19 wherein said threshold amplitude is calibrated by:

determining a minimum reflected amplitude by measuring said reflected amplitude for a joint known to be of maximum quality;

determining a maximum reflected amplitude by measuring said reflected amplitude for a joint known to be of minimum quality; and selecting said threshold amplitude, between said minimum reflected amplitude and said maximum reflected amplitude, to correspond to a desired quality between said minimum quality and said maximum quality.

21. The armature testing station of claim 18 wherein said acoustic beam emitter is an ultrasonic beam emitter.

22. The armature testing station of claim 18 further comprising a vessel containing a medium having a greater acoustic conductivity than air; wherein:

said joint, said emitter and said receiver are immersed in said medium.

23. The armature testing station of claim 22 wherein said medium is a liquid.

24. The armature testing station of claim 23 wherein said liquid medium is substantially electrically nonconductive.

25. The armature testing station of claim 23 wherein said liquid medium is substantially non-oxidizing.

26. The armature testing station of claim 22 further comprising a gripper for removing said armature from said production line, immersing said armature in said vessel for testing, and returning said armature to said production line after testing.

27. The armature testing station of claim 26 wherein said gripper is rotatable to allow successive testing of each of a plurality of joints of an armature.

28. The armature testing station of claim 18 further comprising a gripper for removing said armature from said production line, placing said armature in a location exposed to said emitter and receiver for testing, and returning said armature to said production line after testing.

29. The armature testing station of claim 28 wherein said gripper is rotatable to allow successive testing of each of a plurality of joints of an armature.

30. The armature testing station of claim 18 wherein said acoustic beam emitter and said acoustic receiver are combined in an acoustic probe.

31. A method for testing the quality of a plurality of fused joints of a commutator of an armature of a dynamoelectric machine in succession, each of said fused joints being between a commutator tang and a commutator bar of said commutator, said armature having a longitudinal axis and being gripped by a gripper, said joints being disposed circumferentially around said longitudinal axis of said armature, each of said commutator bars having first and second opposed substantially parallel commutator bar surfaces, each of said tangs having first and second opposed substantially parallel tang surfaces, each of said fused joints being formed between each of said first commutator bar surfaces and each of said first tang surfaces without melting any of said surfaces, said method comprising:

directing an acoustic beam comprising a plurality of pulses from said emitter substantially perpendicular to and substantially toward said longitudinal axis of said armature, at least a portion of one of said plurality of pulses passing through one of said second tang surfaces and reflecting off one or more gaps formed during fusing, said gaps being between said first commutator bar surface and said first tang surface at one of said joints;

rotating said armature around said longitudinal axis of said armature;

measuring said reflected portion of said pulse for each of said joints during said rotating to determine a reflected amplitude profile, said profile having a plurality of maxima;

correlating each of said profile maxima with each of said fused joints;

comparing each of said profile maxima with a predetermined threshold amplitude;

characterizing each of said correlated joints as unacceptable if said correlated profile maximum exceeds said threshold amplitude.

32. The method of claim 31 further comprising the steps of:

determining a minimum reflected amplitude by measuring said reflected amplitude for a joint known to be of maximum quality;

determining a maximum reflected amplitude by measuring said reflected amplitude for a joint known to be of minimum quality; and selecting said threshold amplitude, between said minimum reflected amplitude and said maximum reflected amplitude, to correspond to a desired quality between said minimum quality and said maximum quality.

33. The method of claim 31 wherein said step at directing an acoustic beam comprises directing an ultrasonic beam.

34. The method of claim 31 wherein said directing step comprises directing said beam toward said longitudinal axis of said armature through a medium having a greater acoustic conductivity than air.

35. The method of claim 34 wherein said directing step comprises directing said beam toward said longitudinal axis of said armature through a liquid medium.

36. The method of claim 35 wherein said directing step comprises directing said beam toward said longitudinal axis of said armature through a liquid medium that is substantially electrically nonconductive.

37. The method of claim 36 wherein said directing step comprises directing said beam toward said longitudinal axis of said armature through a liquid medium that is substantially non-oxidizing.

38. Apparatus for testing the quality of a plurality of fused joints of a commutator of an armature of a dynamoelectric machine in succession, each of said fused joints being between a commutator tang and a commutator bar of said commutator, said armature having a longitudinal axis, said joints being disposed circumferentially around said longitudinal axis of said armature, each of said commutator bars having first and second opposed substantially parallel commutator bar surfaces, each of said tangs having first and second opposed substantially parallel tang surfaces, each of said fused joints being formed between each of said first commutator bar surfaces and each of said first tang surfaces without melting any of said surfaces, said apparatus comprising:

an acoustic beam emitter for directing an acoustic beam comprising a plurality of pulses from said emitter substantially perpendicular to and substantially toward said longitudinal axis of said armature, at least a portion of one of said pulses passing through one of said second tang surfaces and reflecting off one or more gaps formed during fusing, said gaps being between said first commutator bar surface and said first tang surface at one of said joints;

a gripper for gripping said armature and for rotating said armature around said longitudinal axis of said armature;

an acoustic receiver for measuring said reflected portion of said pulse for each of said joints during said rotating to determine a reflected amplitude profile, said profile having a plurality of maxima;

an analysis unit for correlating each of said profile maxima with each of said fused joints, comparing each of said profile maxima with a predetermined threshold amplitude, and characterizing each of said correlated joints as unacceptable if said correlated profile maximum exceeds said threshold amplitude.

39. The apparatus of claim 38 wherein said threshold amplitude is determined by:

determining a minimum reflected amplitude by measuring said reflected amplitude for a joint known to be of maximum quality;

determining a maximum reflected amplitude by measuring said reflected amplitude for a joint known to be of minimum quality; and selecting said threshold amplitude, between said minimum reflected amplitude and said maximum reflected amplitude, to correspond to a desired quality between said minimum quality and said maximum quality.

40. The apparatus of claim 38 wherein said acoustic beam emitter is an ultrasonic beam emitter.

41. The apparatus of claim 38 further comprising a vessel containing a medium having a greater acoustic conductivity than air; wherein:

said joint, said emitter and said receiver are immersed in said medium.

42. The apparatus of claim 40 wherein said medium is a liquid.

43. The apparatus of claim 42 wherein said liquid medium is substantially electrically nonconductive.

44. The apparatus of claim 42 wherein said liquid medium is substantially non-oxidizing.

45. The apparatus of claim 38 wherein said acoustic beam emitter and said acoustic receiver are combined in an acoustic probe.

46. A method for testing the quality of a fused joint between a commutator tang and a commutator bar in a commutator of an armature of a dynamoelectric machine, said commutator bar having first and second opposed substantially parallel commutator bar surfaces, said tang having first and second opposed substantially parallel tang surfaces, said fused joint being formed between said first commutator bar surface and said first tang surface without melting any of said surfaces, said method comprising:

directing an acoustic beam comprising at least one pulse having a frequency of about 20 MegaHertz toward said second tang surface along an axis substantially perpendicular to said second tang surface, at least a portion of said pulse passing through said tang and reflecting off one or more gaps formed during fusing, said gaps being between said first commutator bar surface and said first tang surface at said joint;

measuring said reflected portion of said pulse to determine a reflected amplitude;

comparing said reflected amplitude to a predetermined threshold amplitude; and characterizing said joint as having at least one gap having a depth greater than about 0.005 mm in a direction perpendicular to the plane of the joint if said reflected amplitude exceeds said threshold amplitude.

47. The method of claim 46 further comprising the steps of:

determining a minimum reflected amplitude by measuring said reflected amplitude for a joint known to be of maximum quality;

determining a maximum reflected amplitude by measuring said reflected amplitude for a joint known to be of minimum quality; and selecting said threshold amplitude, between said minimum reflected amplitude and said maximum reflected amplitude, to correspond to a desired quality between said minimum quality and said maximum quality.

48. The method of claim 46 wherein said step at directing an acoustic beam along said axis comprises directing an ultrasonic beam along said axis.

49. The method of claim 46 wherein said directing step comprises directing said beam toward said second tang surface through a medium having a greater acoustic conductivity than air.

50. The method of claim 49 wherein said directing step comprises directing said beam toward said second tang surface through a liquid medium.

51. The method of claim 50 wherein said directing step comprises directing said beam toward said second tang surface through a liquid medium that is substantially electrically nonconductive.

52. The method of claim 51 wherein said directing step comprises directing said beam toward said second tang surface through a liquid medium that is substantially non-oxidizing.

* * * * *